United States Patent
Harnack

(10) Patent No.: US 8,840,575 B2
(45) Date of Patent: Sep. 23, 2014

(54) ORTHOTIC FITTING HAVING A KNEE GUIDE JOINT

(75) Inventor: Roland Harnack, Eisenärtz (DE)

(73) Assignee: Spoerer AG, Ingolstadt (DE)

( * ) Notice: Subject to any disclaimer, the term of this patent is extended or adjusted under 35 U.S.C. 154(b) by 265 days.

(21) Appl. No.: 13/201,860

(22) PCT Filed: Feb. 15, 2010

(86) PCT No.: PCT/EP2010/000915
§ 371 (c)(1),
(2), (4) Date: Oct. 28, 2011

(87) PCT Pub. No.: WO2010/094444
PCT Pub. Date: Aug. 26, 2010

(65) Prior Publication Data
US 2012/0035517 A1   Feb. 9, 2012

(30) Foreign Application Priority Data
Feb. 17, 2009   (DE) .................. 10 2009 009 250

(51) Int. Cl.
*A61F 5/00*   (2006.01)

(52) U.S. Cl.
USPC ............ 602/16; 602/5; 602/23; 602/26

(58) Field of Classification Search
CPC ........ A61F 5/01; A61F 5/0106; A61F 5/0123
USPC .............. 602/5, 16, 23, 26; 128/882
See application file for complete search history.

(56) References Cited

U.S. PATENT DOCUMENTS

| 4,523,585 | A | | 6/1985 | Lamb et al. | |
|---|---|---|---|---|---|
| 4,628,916 | A | | 12/1986 | Lerman et al. | |
| 4,699,129 | A | * | 10/1987 | Aaserude et al. | 602/16 |
| 4,821,707 | A | | 4/1989 | Audette | |
| 5,022,391 | A | * | 6/1991 | Weidenburner | 602/16 |
| 6,979,304 | B2 | | 12/2005 | Nijenbanning et al. | |

FOREIGN PATENT DOCUMENTS

| DE | 19904554 A1 | 8/2000 |
|---|---|---|
| DE | 10 2004 038 191 A1 | 3/2006 |
| DE | 60124510 T2 | 7/2007 |
| DE | 20200704602 U1 | 4/2008 |
| EP | 0 267 999 A1 | 5/1988 |
| EP | 0 546 331 A1 | 6/1993 |
| WO | 2009049593 A1 | 4/2009 |

* cited by examiner

*Primary Examiner* — Patricia Bianco
*Assistant Examiner* — Camtu Nguyen
(74) *Attorney, Agent, or Firm* — Laurence A. Greenberg; Werner H. Stemer; Ralph E. Locher

(57) ABSTRACT

An orthotic fitting has a knee guide joint and two leg parts, which can be rigidly connected to a lower leg mounting part and an upper leg mounting part, respectively. The knee guide joint has a four-joint arrangement having four axially parallel joints, arranged so that, at the ends of the leg parts in each case angled lever parts are configured, each having two swivel bearings arranged at a distance from each other, and that in each case the swivel bearing of an angled lever part closer to the leg is connected to the swivel bearing of the other angled lever part further from the leg, in each case by a swivel element.

14 Claims, 7 Drawing Sheets

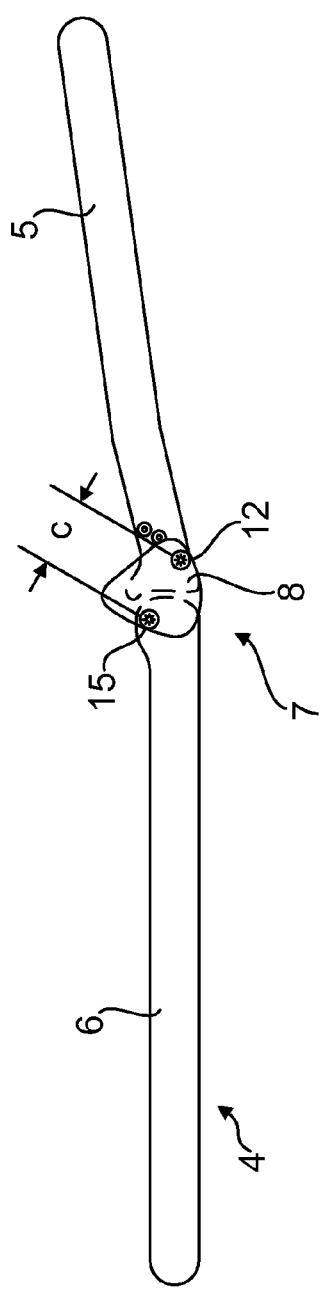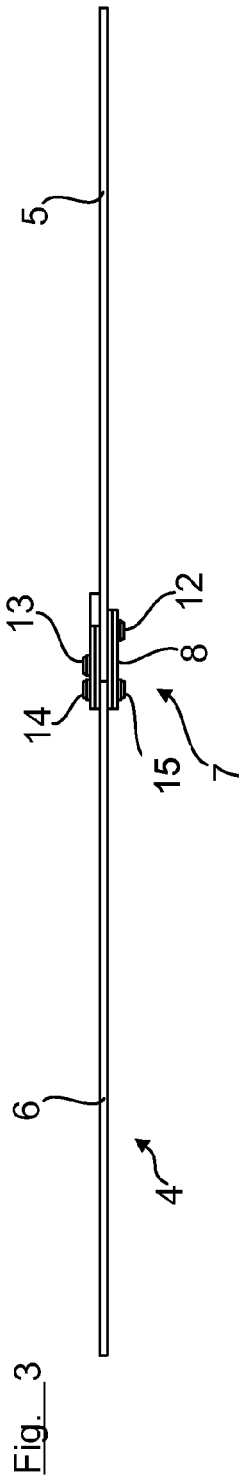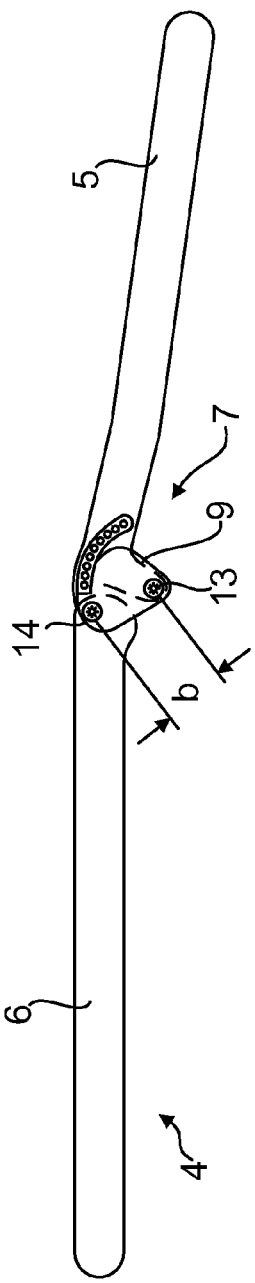

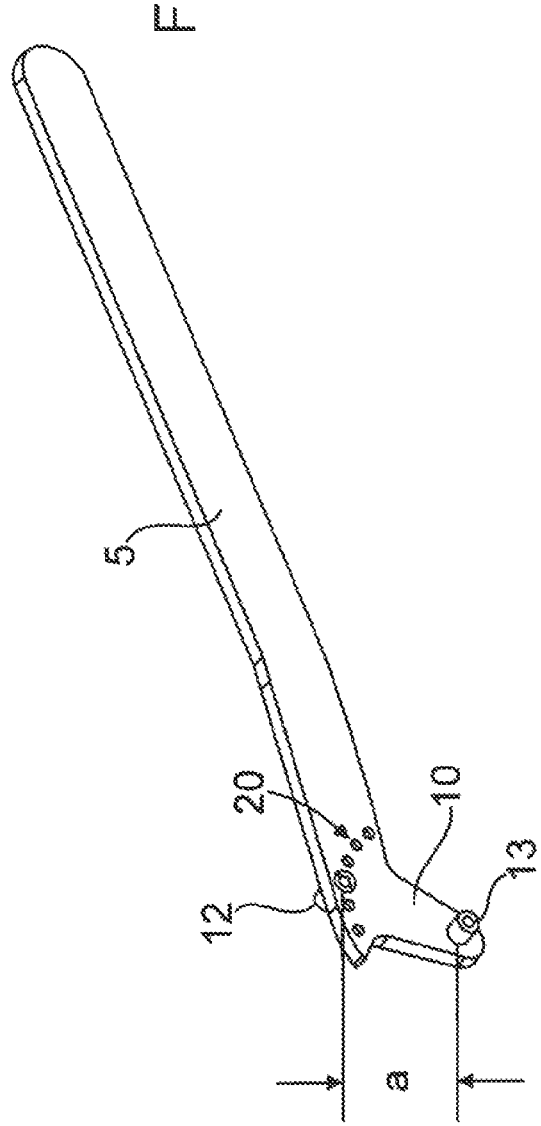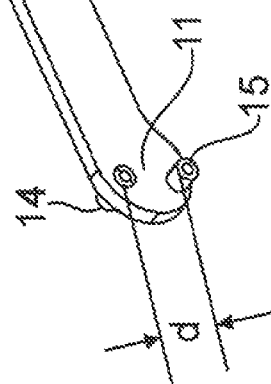

ORTHOTIC FITTING HAVING A KNEE GUIDE JOINT

BACKGROUND OF THE INVENTION

Field of the Invention

The invention relates to an orthotic fitting having a knee guide joint, with which it is possible, unilaterally with one fitting, or bilaterally with opposite fittings, to connect a lower leg mounting part and an upper leg mounting part of the orthosis to each other in an articulated manner as a knee joint support. For this purpose, such a fitting has two leg parts, which can be rigidly connected to the lower leg mounting part and to the upper leg mounting part, respectively, and of which the leg ends directed toward each other are component parts of the knee guide joint. The expressions lower leg mounting part and upper leg mounting part are understood in general as all devices, such as shell parts, strap elements, cuffs, bandages, etc, with which an orthotic fitting can be secured and fixed with its two leg parts in a predetermined position on the lower leg and upper leg of a patient.

In generally known knee orthoses of this kind, the knee guide joints of the orthotic fittings are in most cases designed as simple rotary joints. The range of pivoting is optionally determined and limited by abutments. For example, such knee orthoses are applied after cruciate ligament surgery, as a result of which the relative movement between lower leg and upper leg is possible only within the context of the kinematics of the knee orthosis in association with a stabilization of the knee.

The pivot geometry of the human knee corresponds not to a rotary joint but to a sliding pivot joint in which the pivot axis shifts spatially depending on the pivot angle. The pivoting movement forced on the knee by the knee orthosis via the rotary joints of the orthotic fittings does not therefore correspond to the pivoting movement of the knee, such that the knee, from which the load is intended to be taken up by the orthosis, is subjected unfavorably to constraining forces in certain ranges of pivoting. These constraining forces can be slightly reduced in a manner known per se if the rotary joints of the orthosis are positioned slightly above the knee joint, although unfavorable constraining forces still act on the knee joint in this arrangement too.

In order to provide an improvement in this respect, polycentric knee orthoses (DE 199 33 197 B4) with a joint mechanism are therefore already known which have two spaced-apart pivot axes for the pivotable bearing of the distal leg and the proximal leg of an orthotic fitting. In addition, the leg ends mesh with each other via teeth, and adjustable abutments are provided for limiting the range of pivoting. Knee orthoses of this kind with two axes are intended, with their pivot geometry, to simulate the natural sequence of movement during flexion of the knee joint and to do so better than the knee orthoses described above with only single-axis orthotic fittings. On the one hand, however, constraining forces still act on the knee joint in this case too, since once again the simulation of the natural movement is incomplete, and, on the other hand, the orthotic fitting with a toothed joint is complex and expensive.

BRIEF SUMMARY OF THE INVENTION

The object of the invention is to propose an orthotic fitting with a knee guide joint in which the kinematics substantially correspond to the natural sequence of movement of a knee joint and which additionally permits a stable, functional and inexpensive set-up.

According to the invention, the knee guide joint is designed as a four-joint arrangement with four axially parallel joints. For this purpose, at the ends of the legs of the fitting, in each case angled lever parts are formed, each having two pivot bearings spaced apart from each other. The pivot bearing of an angled lever part nearer the leg is connected to the pivot bearing of the other angled lever part further from the leg, in each case by a pivot element, such that, in addition to the angled lever parts mounted rigidly on the two legs of the fitting, two pivot elements articulated in the above manner are also used.

With a four-joint arrangement of this kind, pivoting movements between the legs of the fitting can be changed, and in particular substantially adapted to natural movements of the knee joint, by dimensioning of the spacings between the pivot bearings. Since the four-joint arrangement according to the invention merely requires simple pivot bearings that can be realized easily by way of bores and pivot pins, the set-up is simple and production is correspondingly inexpensive.

In particularly preferred dimensioning, the spacing (a) of the two pivot bearings located on a first angled lever part of a first, preferably lower, distal leg part corresponds to the spacing (b) of the two pivot bearings between the joint bearing remote from the leg on the first angled lever part and the pivot bearing near the leg on the second angled lever part of the second, preferably upper, proximal leg part and therefore corresponds to the spacing of the associated pivot bearings on a first pivot element. In addition, the spacing (a) of the two pivot bearings on the first angled lever corresponds, like the above-mentioned spacing (b), to the spacing (c) of the two pivot bearings between the pivot bearing remote from the leg on the second angled lever part and the pivot bearing near the leg on the first angled lever part and therefore corresponds to the corresponding spacing of the pivot bearings on the second pivot element. Whereas the abovementioned spacings are equal in size, the spacing (d) of the two pivot bearings on the second angled lever part corresponds to only half the spacing (a) of the two pivot bearings on the first angled lever part. In connection with a four-joint arrangement, the comments made here concerning three equal spacings and a half-spacing result in a substantially precise simulation of the sequence of movement of a natural knee joint, wherein fairly small tolerances in the indicated spacings can still give good results.

According to another feature of the invention, a further optimization in adaptation can be achieved by the fact that the connecting line between the pivot bearings on the second angled lever part extends perpendicular to the leg direction of the second leg part, but the connecting line between the pivot bearings on the first angled lever part extends at an angle of greater than 90°, preferably of ca. 105°, with respect to the leg direction of the first leg part. If necessary, the first leg part can also extend curving away at a distance from the knee guide joint.

With the sizes for the spacings a, b, c according to the invention, namely of 22 mm to 30 mm, preferably of 26 mm, and correspondingly a spacing size d of 11 mm to 15 mm, preferably 13 mm, the movement adaptation to a natural knee joint is possible in a particularly optimal way.

According to the invention, for a design with a favorable weight and a high degree of stability, the leg parts, including the angled lever parts, should be made of a flat material, preferably of stainless steel material. In addition, the pivot elements should be designed as disk parts, the latter bearing on the flat angled lever parts facing each other, such that it is possible, with little outlay, to obtain good longitudinal guiding in all pivoting positions.

In a development according to a further of the invention, these disk parts are designed in two layers, with a stable outer face composed of a stainless steel layer and with a corresponding inner face composed of a brass layer, and the two layers are adhesively bonded. The contact connection displaceable during the pivoting movement is produced via the brass layer, and, for smooth-running pivoting, the brass layer advantageously acts as a self-lubricating coat.

A simple concrete design of the pivot bearings is indicated by the features of the invention. Thus, protruding bearing bushes are mounted on the angled lever parts and are plugged with a form fit into the disk parts through the associated bores, wherein the bearing bush lengths correspond with slight oversize to the thicknesses of the disk parts. The bearing bushes contain axial screw holes for receiving screws with screw heads, which cover bores of the disk parts and bear on the disk parts from the outside. In this way, smooth-running and maintenance-free pivot bearings can be achieved in conjunction with a simple set-up of the knee guide joint.

According to another feature of the invention, it is proposed to arrange associated abutments on at least one of the leg parts and on a pivot element movable relative thereto, in particular on a disk part, which abutments can be releasable and displaceable and limit the pivoting movement of the legs in a predetermined manner.

Specifically, according to another feature of the invention, an abutment can be mounted laterally on the first leg part such that, during a pivoting movement of the leg to a more extended position, the abutment is movable along the edge of the first disk part as far as an abutment located there.

In another embodiment according to the invention, for improved longitudinal guiding, a channel-shaped guide groove, if appropriate in conjunction with an abutment, can be arranged laterally on the first leg part, in which guide groove a disk edge of the first disk part is guided during a pivoting movement of the leg. According to another claim, the guide wall surface directed toward and bearing on the surface of the disk part can be designed in two layers with a self-lubricating brass layer.

According to another feature of the invention, in a manner known per se, the leg parts of the fitting can be mounted rigidly and non-releasably on the lower leg mounting part and on the upper leg mounting part or mounted rigidly and releasably on rail parts located there.

The invention is explained in more detail with reference to a drawing, in which:

BRIEF DESCRIPTION OF THE SEVERAL VIEWS OF THE DRAWING

FIG. 2 shows a side view of an orthotic fitting;

FIG. 3 shows a plan view of the orthotic fitting according to FIG. 2;

FIG. 4 shows a side view of the orthotic fitting according to FIG. 2, from the opposite side;

FIG. 8 shows a perspective view of the first leg part with the first angled lever part;

FIG. 9 shows a perspective view of the second leg part with the second angled lever part;

DESCRIPTION OF THE INVENTION

Figure 1:
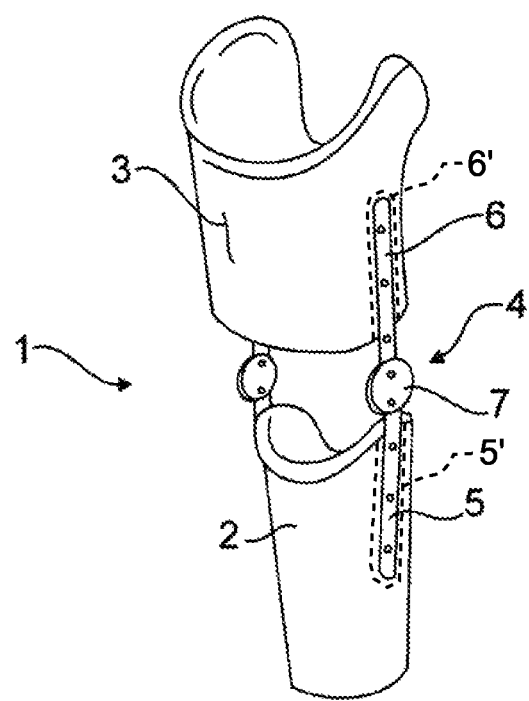
FIG. 1 shows a schematic view of a knee orthosis having bilateral orthotic fittings with knee guide joints.

FIG. 1 is a schematic view of a knee orthosis 1 with a lower leg mounting part 2 and an upper leg mounting part 3, which mounting parts are connected bilaterally in an articulated manner by orthotic fittings 4. Each orthotic fitting 4 consists of a lower, distal leg part 5 and of an upper, proximal leg part 6 made of flat steel, wherein the leg parts 5, 6 are rigidly connected to the associated mounting parts 2, 3, or they are mounted rigidly and releasable on rail parts 5' and 6', respectively, and have a connection to each other via a knee guide joint 7, which will be described in more detail below.

Figure 5:
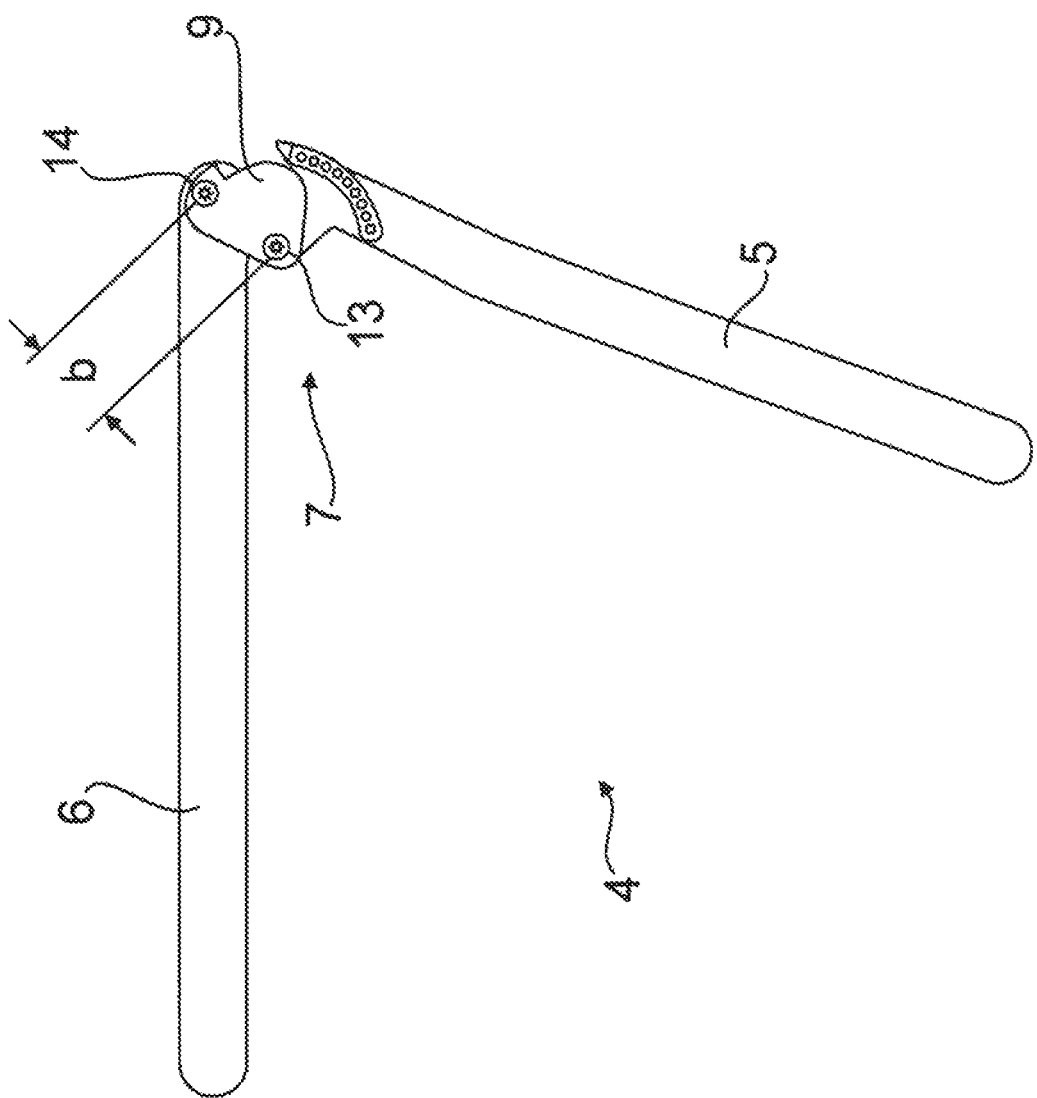
FIG. 5 shows a view corresponding to FIG. 4, with pivoted leg parts.

FIGS. 2 to 5 show a fully mounted orthotic fitting 4 in different views, in each case with a first, distal leg part 5 and a second, proximal leg part 6 and the knee guide joint 7, with FIG. 2 showing a plan view of a second disk part 8, and FIGS. 4 and 5 showing plan views of a first disk part 9. In FIGS. 2 and 4, the end contour of the adjoining leg parts 5, 6 is indicated in each case by broken lines under the disk parts 8 and 9. This can be seen more exactly from FIGS. 8 and 9, in which the first, distal leg part 5 and the second, proximal leg part 6 are shown as individual parts.

On the first leg part 5, the end of the leg toward the joint is designed with a first angled lever part 10, and the second, proximal leg part 6 with a second angled lever part 11, wherein the functions of the angled levers are each formed principally by spaced-apart pivot bearing elements 12, 13 on the first angled lever part 10 and pivot bearing elements 14, 15 on the second angled lever part 11. The corresponding reference signs 12 to 15 denote in all the figures the associated bearing bores on the disk parts 8, 9 and also the pivot bearing locations (in FIGS. 12 and 13).

Figure 6:
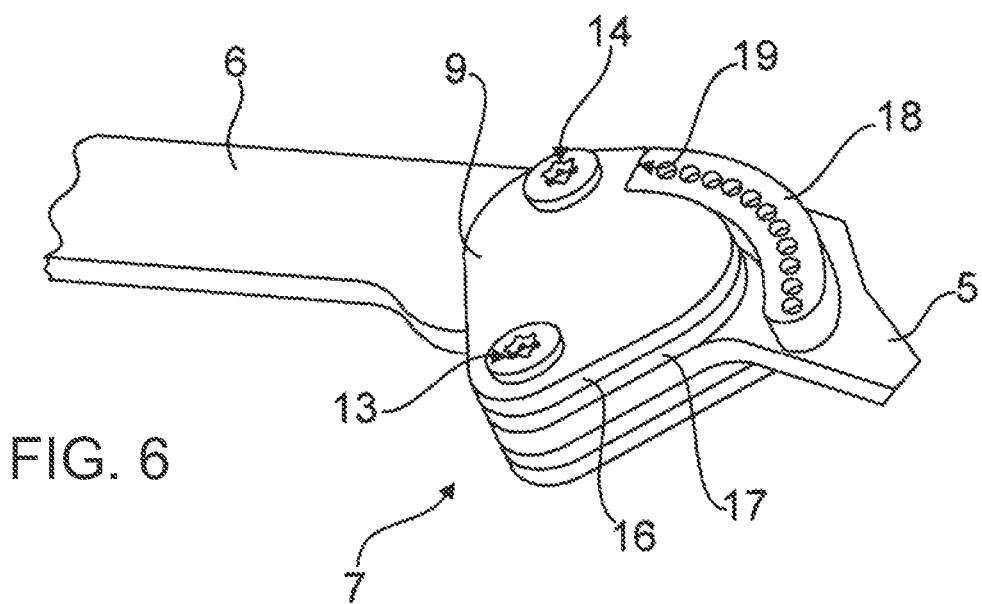
FIG. 6 shows an enlarged perspective view of the knee guide joint from a direction according to FIG. 4.
Figure 7:
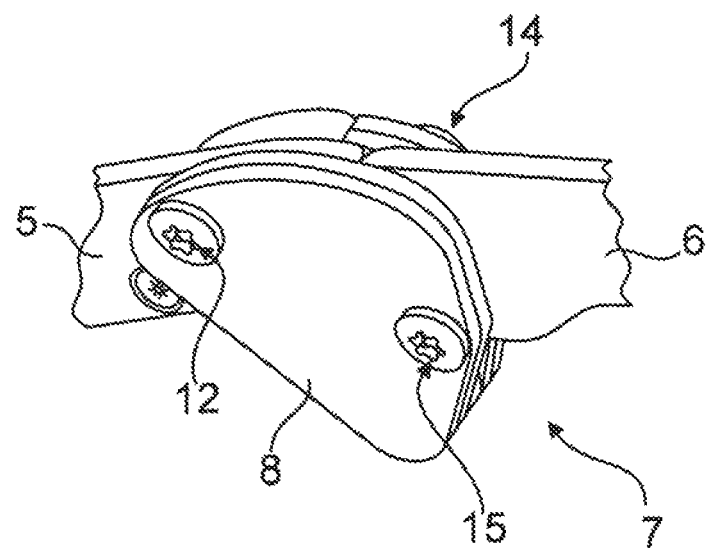
FIG. 7 shows an enlarged perspective view of the knee guide joint from the direction according to FIG. 2.
Figure 10:
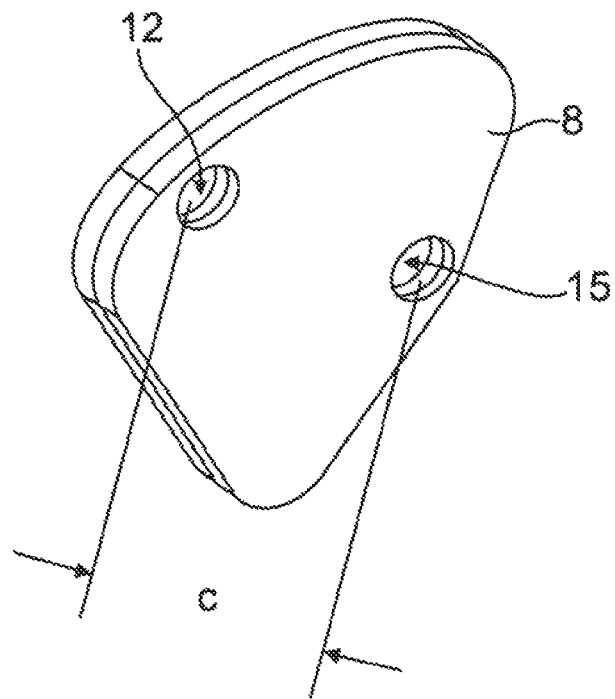
FIG. 10 shows an enlarged perspective view of the second disk part.

The pivot bearing elements 12 to 15 on the leg parts 5, 6 (see FIGS. 8, 9) are designed as protruding bearing bushes, which are plugged into the disk parts 8, 9 (see FIGS. 10, 11) through correspondingly assigned bores. The bearing bush lengths correspond with slight oversize to the thicknesses of the disk parts. The bearing bushes contain axial screw holes for receiving screws, of which the screw heads cover the bores of the disk parts 8, 9 and bear thereon from the outside (see FIGS. 6, 7).

The disk parts 8, 9 each bear from the outside on the angled lever parts 10, 11 and form the pivot elements for the four-joint arrangement depicted. The disk parts 8, 9 are each designed in two layers, with an outer stable stainless steel layer 16 and an inner brass layer 17, as is indicated for example by reference signs 16, 17 in FIGS. 6, 11. The two layers are adhesively bonded.

Figure 11:
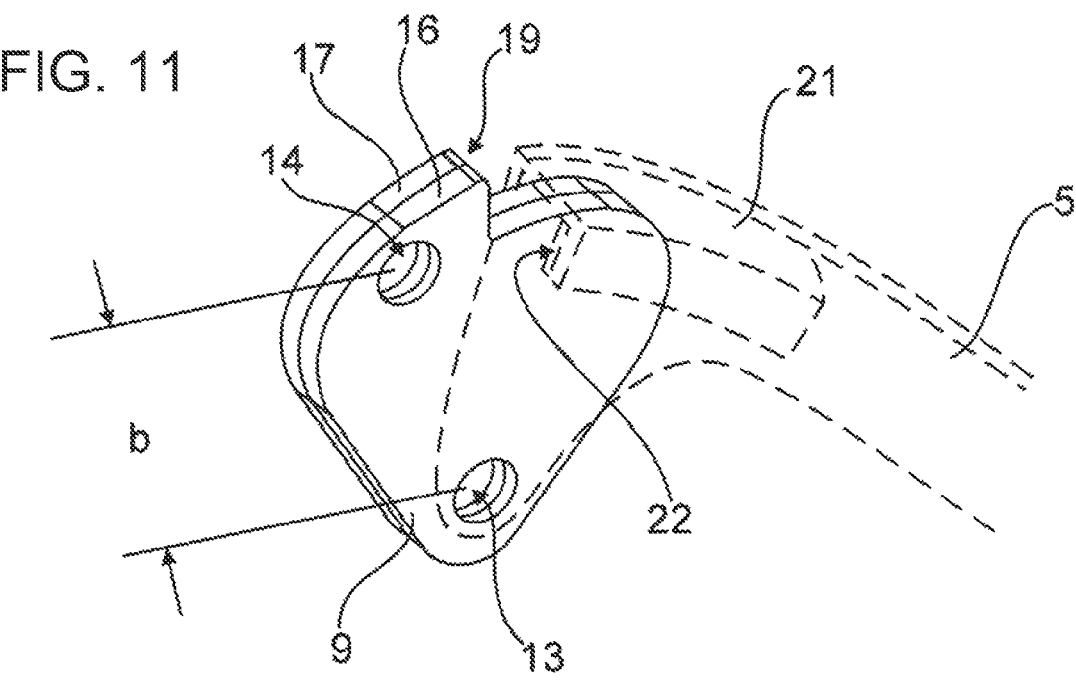
FIG. 11 shows a corresponding view of the first disk part, with a guide indicated by broken lines.

On the first leg part 5, in the area of the pivot bearing, an abutment bracket 18 is mounted which cooperates with an associated abutment shoulder 19 on the first disk part 9 in order to limit the extension of the fitting. If necessary, the abutment bracket 18 can be arranged here on an associated row of bores 20 on the first leg part 5 (FIG. 8). As an alternative to the abutment bracket 18, an abutment and guide channel 21, indicated by broken lines in FIG. 11, is rigidly mounted laterally on the first leg part 5 and at one end cooperates with the abutment shoulder 19 in the abutment function and at the other end forms an edge-side guide for the disk part 9. Here too, the inner guide wall surface of the channel is provided with a brass layer 22.

The function and the sequence of movement of the knee guide joint are explained with reference to FIGS. 12 and 13 and are determined by the constrained movement of the four-joint arrangement with the pivot bearings 12 to 15. As can be seen in particular from FIG. 12, the spacing of the pivot bearings 12, 13 on the first angled lever part 10 of the pivot part 5, designated as spacing a, is equal to the spacing b of the bearings 13, 14 on the first disk part 9 and to the spacing c of the pivot bearings 12, 15 on the second disk part 8. By contrast, the spacing d of the two pivot bearings 14, 15 on the second angled lever part 11 of the second leg part 6 is only half as great. In a specific embodiment, the spacings a, b, c are 26 mm and the spacing d 13 mm. For clarity, FIGS. 12 and 13 are also shown on the scale 2:1.

The connecting line between the pivot bearings 14, 15 on the second angled lever part extends perpendicular to the leg direction of the second leg part 6. By contrast, the connecting line between the pivot bearings 12, 13 on the first angled lever part 10 of the first leg part 5 extends at a greater angle 23 of ca. 105° to the leg direction of the first leg part 5.

Figure 12:
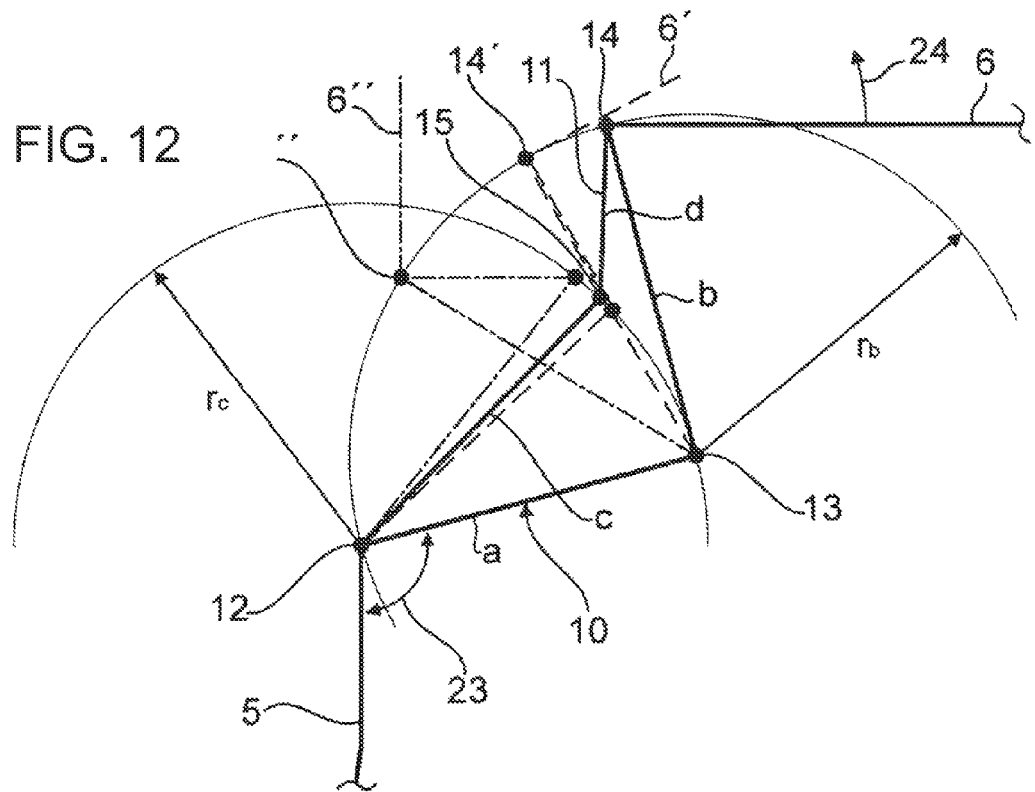
FIG. 12 shows a representation of the kinematics of the knee guide joint during an upward pivoting movement.
Figure 13:
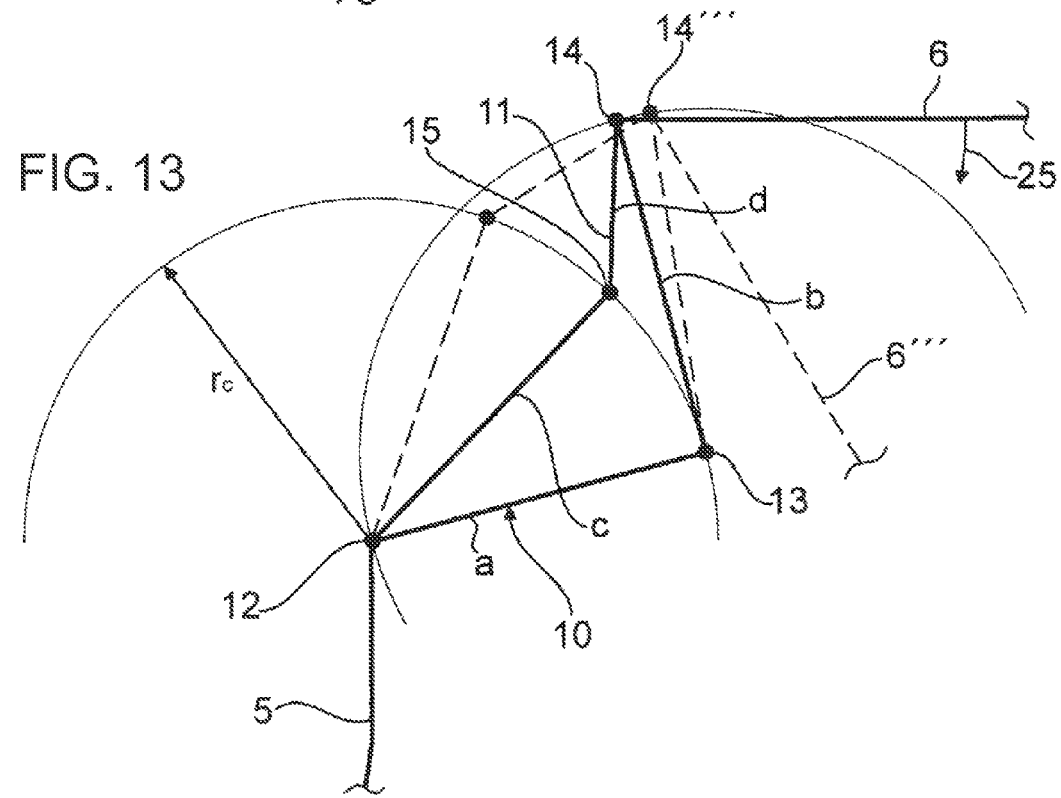
FIG. 13 shows a representation, corresponding to FIG. 12, during an inward pivoting movement of the knee guide joint.

In each of FIGS. 12 and 13, a continuous thick line schematically indicates the initial state of the four-joint arrangement when the two leg parts 5, 6 lie at a right angle to each other.

In accordance with the arrow 24 in FIG. 12, the leg part 6 is now to be pivoted upward to a more extended position while the position of the leg part 5 is maintained. The pivot bearing 15 necessarily moves along the plotted arc of a circle with the radius rc, and the pivot bearing 14 necessarily moves along the arc of a circle with the radius rb. The position on these arcs of a circle is determined by the coupling via the disk parts 8, 9 in connection with the bearing spacing d.

A slightly upwardly pivoted position 6' of the leg part 6 is indicated by broken lines in FIG. 12, where it can be seen that the pivot bearing 14 has migrated forward to the position 14'. Upon further extension of the leg part to the position 6" indicated by dot-and-dash lines, the associated pivot bearing 14 has shifted further forward and slightly downward into the position 14".

In accordance with the arrow 25 in FIG. 13, the leg part 6 is pivoted downward into the position 6'" indicated by broken lines, while the position of the leg part 5 is maintained, as a result of which the pivot bearing 14 has moved slightly rearward to the position 14'" on the arc of a circle with the radius rb at approximately the same height.

The pivot geometry explained above provides substantial simulation of the natural movement of the knee joint.

The invention claimed is:

1. A knee orthosis for a leg, comprising:
a lower leg mounting part and an upper leg mounting part;
a knee guide joint, having at least one orthotic fitting unilaterally connecting said lower leg mounting part and said upper leg mounting part in an articulated manner forming a knee joint support, said orthotic fitting having two leg parts rigidly connected to said lower leg mounting part and said upper leg mounting part, respectively, said leg parts each having leg ends directed toward each other; wherein
said knee guide joint including a four-joint arrangement having four axially parallel joints;
first and second angled lever parts respectively disposed at each of said leg ends and having at least two pivot bearings spaced apart from each other; and
at least a first pivot element connecting a first of said pivot bearings of the angled lever part being located nearer the leg to a second of said pivot bearings of the other of said angled lever parts being located further from the leg;
a first spacing (a) of said pivot bearings on said first angled lever part of a first lower distal one of said leg parts, being equal to a second spacing (b) of said pivot bearings on said first pivot element between one of said pivot bearings remote from the leg on said first angled lever part and another of said pivot bearings near the leg on said second angled lever part of a second upper proximal one of said leg parts;
a third spacing (c) of said pivot bearings on a second pivot element between the pivot bearing remote from the leg on said second angled lever part and the pivot bearing near the leg on said first angled lever part being equal to the first spacing (a); and
a fourth spacing (d) of said pivot bearings on said second angled lever part being equal to half the first spacing (a).

2. The orthosis fitting according to claim 1, wherein:
a connecting line between said pivot bearings on said second angled lever part extends perpendicular to a leg direction of a second of said leg parts; and
a connecting line between said pivot bearings on said first angled lever part extends at an angle of greater than 90° with respect to a leg direction of a first of said leg parts.

3. The orthosis according to claim 1, wherein: the first, second, and third spacings lie within a range of 22 mm to 30 mm, and the fourth spacing lies within a range of 11 mm to 15 mm.

4. The orthosis according to claim 1, wherein:
said leg parts and said angled lever parts are made of a flat stainless steel material;
said first and second pivot elements are first and second disk-shaped parts which cover and bear on both sides on said angled lever parts facing each other;
said first disk part, from a direction of a first outer face, is attached pivotably to said pivot bearing located further from the leg on said first angled lever part and to said pivot bearing located nearer the leg on said second angled lever part; and
said second disk part, from a direction of a second outer face opposite the first outer face, is attached pivotably to said pivot bearing further from the leg on said second angled lever part and to said pivot bearing nearer the leg on said first angled lever part.

5. The orthosis according to claim 4, wherein: said disk parts each have a plurality of layers, including an outer face of stainless steel and a corresponding inner face of brass layer, and said layers are adhesively bonded.

6. The orthosis according to claim 4, wherein: said pivot bearings comprise protruding bearing bushings which fit into associated bores on said disk parts, said bearing bushings having lengths that correspond with slight oversize to a thicknesses of said disk parts, and said bearing bushings have axial screw holes for receiving screws with screw heads which cover the bores of said disk parts and bear on said disk parts from the outside.

7. The orthosis according to claim 4, further including: abutments which interact and limit pivoting movement of the leg located on at least one of said leg parts and on said at least first pivot element.

8. The orthosis according to claim 7, wherein: an abutment is displaceably mounted laterally on a first of said leg parts, such that, during a pivoting movement of the leg to a more extended position, said abutment is movable along an edge of a first of said disk parts to another said abutment to limit the pivoting movement.

9. The orthosis according to claim 4, further including: a channel-shaped guide groove, for cooperation with an abutment arranged laterally on a first of said leg parts, wherein a disk edge of a first of said disk parts is guided in said guide groove during a pivoting movement of the leg.

10. The orthosis according to claim 9, wherein: the guide groove has a guide wall surface directed toward and bearing on a surface of said first of said disk parts, and said guide wall surface comprises multiple layers including a brass layer.

11. The orthosis according to claim 1, wherein: said leg parts are mounted rigidly and non-releasably on said lower leg mounting part and said upper leg mounting part.

12. The orthosis according to claim 1, wherein said leg parts are mounted rigidly on said lower leg mounting part and said upper leg mounting part respectively.

13. The orthosis according to claim 1, wherein: said knee joint has two opposed orthotic fittings bilaterally connected between said lower leg mounting part and said upper leg mounting part.

14. The orthosis according to claim 1, wherein: said leg parts are mounted rigidly and releasably on rail parts disposed on said lower leg mounting part and said upper leg mounting part.

* * * * *